(12) United States Patent
Daly

(10) Patent No.: US 7,502,653 B2
(45) Date of Patent: Mar. 10, 2009

(54) COCHLEAR IMPLANT HAVING PATIENT-SPECIFIC PARAMETER STORAGE

(75) Inventor: Christopher Newton Daly, Bilgoa Plateau N.S.W. (AU)

(73) Assignee: Cochlear Limited, Lane Cove (AU)

( * ) Notice: Subject to any disclaimer, the term of this patent is extended or adjusted under 35 U.S.C. 154(b) by 376 days.

(21) Appl. No.: 10/333,676

(22) PCT Filed: Jul. 6, 2001

(86) PCT No.: PCT/AU01/00811

§ 371 (c)(1),
(2), (4) Date: Jun. 27, 2003

(87) PCT Pub. No.: WO03/003956

PCT Pub. Date: Jan. 16, 2003

(65) Prior Publication Data

US 2004/0024429 A1    Feb. 5, 2004

(51) Int. Cl.
*H04R 25/00* (2006.01)
*G10L 21/02* (2006.01)

(52) U.S. Cl. ..................................... 607/57
(58) Field of Classification Search ............ 607/59, 607/55–57; 604/891.1
See application file for complete search history.

(56) References Cited

U.S. PATENT DOCUMENTS

| | | | |
|---|---|---|---|
| 5,569,307 A * | 10/1996 | Schulman et al. | 607/56 |
| 5,571,148 A * | 11/1996 | Loeb et al. | 607/57 |
| 5,690,690 A | 11/1997 | Nappholz et al. | |
| 5,800,473 A | 9/1998 | Faisandier | |
| 5,817,137 A | 10/1998 | Kaemmerer | |
| 5,891,180 A | 4/1999 | Greeninger et al. | |
| 5,941,905 A | 8/1999 | Single | |
| 6,195,585 B1 * | 2/2001 | Karunasiri et al. | 607/57 |
| 6,198,971 B1 * | 3/2001 | Leysieffer | 607/55 |
| 6,243,608 B1 | 6/2001 | Pauly et al. | |
| 6,740,075 B2 * | 5/2004 | Lebel et al. | 604/891.1 |
| 7,346,397 B2 * | 3/2008 | Money et al. | 607/57 |

FOREIGN PATENT DOCUMENTS

| | | |
|---|---|---|
| DE | 19915846 | 8/2000 |
| EP | 0 730 882 A2 | 9/1996 |
| WO | WO00/72917 A1 | 12/2000 |
| WO | 01/06810 | 1/2001 |
| WO | 01/13991 | 3/2001 |

OTHER PUBLICATIONS

International Search Report; Not Yet Published; Application No. PCT/AU01/00811; Filed Jul. 6, 2001; Inventor: Christopher N. Daly; Applicant: Cochlear Limited.
EPO Official Communication. EP 01 951 205.2. Jan. 23, 2008.

* cited by examiner

*Primary Examiner*—George R Evanisko
*Assistant Examiner*—Michael Kahelin
(74) *Attorney, Agent, or Firm*—Connolly Bove Lodge & Hutz LLP

(57) ABSTRACT

An arrangement for implanted medical devices in which the implant (20) includes certain parameters (21) stored in memory. Upon initialisation, these parameters are downloaded to the external component (30). This allows for simpler changes to the external device, or for a generic external device to be used. A particular application is to Cochlear implants.

69 Claims, 2 Drawing Sheets

COCHLEAR IMPLANT HAVING PATIENT-SPECIFIC PARAMETER STORAGE

FIELD OF THE INVENTION

The present invention relates to implanted medical devices, for example cochlear implants, which combine an implanted device with an external, continuously linked device to provide the required functionality.

BACKGROUND ART

Medical devices of various types operate using an implanted component, and an external unit which is required to be linked to the implanted component, for example by an RF or inductive link, to provide the required functionality. The following discussion will be principally in the context of cochlear implants, but other similar issues arise for devices such as spinal, visual or other neural stimulators, and other medical implant applications.

In the case of cochlear implants, the system is generally configured as an external speech processor, and an implanted receiver/stimulator device. The internal device includes an electrode array-for providing electrical stimuli to the cochlea, electrical circuitry to generate the stimuli, and a means for receiving signals and power from the external speech processor. One arrangement, generally used in devices manufactured by the applicant, uses an inductive link to transfer power and data between the external speech processor unit and the implanted receiver/stimulator device. For the purposes of this invention however, the precise mechanism used is not presently relevant.

Conventionally cochlear implant devices have been arranged such that the implanted unit responds to commands from a compatible processor, but does not store patient specific data or identification codes in such a way so as to exclude the implanted unit responding to any processor unit. In conventional systems the patient specific data and programming is stored in the external speech processor and there is no data retained in the implant when it is powered down.

One issue with such devices is that in some situations, for example in a facility for the hearing impaired, it is possible for users to inadvertently swap speech processors. Each speech processor will contain a set of data specific to each individual—for example, speech processing strategies, stimulus coding strategies and electrode mapping parameters. If the wrong speech processor is used for a patient, then the use of the incorrect parameters will cause at best poor speech perception by the user, and at worst may cause pain and discomfort. Present cochlear implant systems do not incorporate mechanisms to prevent such a problem arising.

Similarly, if the speech processor is lost or damaged, the only record of the appropriate parameters for the patient is stored at the clinic which provided the programming for the processor. The clinician needs to then access the patients records and identify the implant serial number to initiate a programming session. If this is not readily available, then a new speech processor must be programmed from the beginning, which is a complex and time consuming process. Similar issues arise for other implanted devices which use an external component to provide ongoing data to an implant.

With this in mind, one object of the present invention is to provide an implanted device which allows for desired operation of the device through use of a compatible generic external component.

A further object of the present invention is a system which prevents inadvertent operation of an implanted medical device with incorrect parameters.

Yet a further object of the present invention is a system which allows for a simple process of exchanging external processors and accessing of patient specific data.

SUMMARY OF THE INVENTION

Broadly, the present invention provides a change in the paradigm of where the patient specific data is stored. Instead of the implanted device being essentially undifferentiated and the external processor customised, the implanted device is used to store the user specific parameters, which are downloaded by the external processor each time it is first brought into operational mode. As a consequence, the external processor need not be customised, and in a preferred implementation is essentially a generic device, which is customised by the parameters downloaded from the implant each time it is turned on. Additionally, during operation the external processor is preferably continually checking that it is still connected to the same implant, for example by periodic interrogation of the implant and receiving an expected serial number.

This approach allows for the external processor to be customised to the active implant, regardless of which user currently is in possession, subject of course to compatibility of the external processor and the implant. This also allows, for example, simplified use of a replacement external processor. The necessary parameters are carried in a suitable memory device in the implant, and uploaded at the start of operation to the external processor. This may be readily achieved by using the telemetry link which already exists in many available devices. The processor may also detect the type or model of the implant, and so select the appropriate operational mode.

DETAILED DESCRIPTION

The present invention will be explained principally in the context of cochlear implants. However, it will be appreciated by those skilled in the art that the same principle is readily implemented in other applications.

Figure 1:
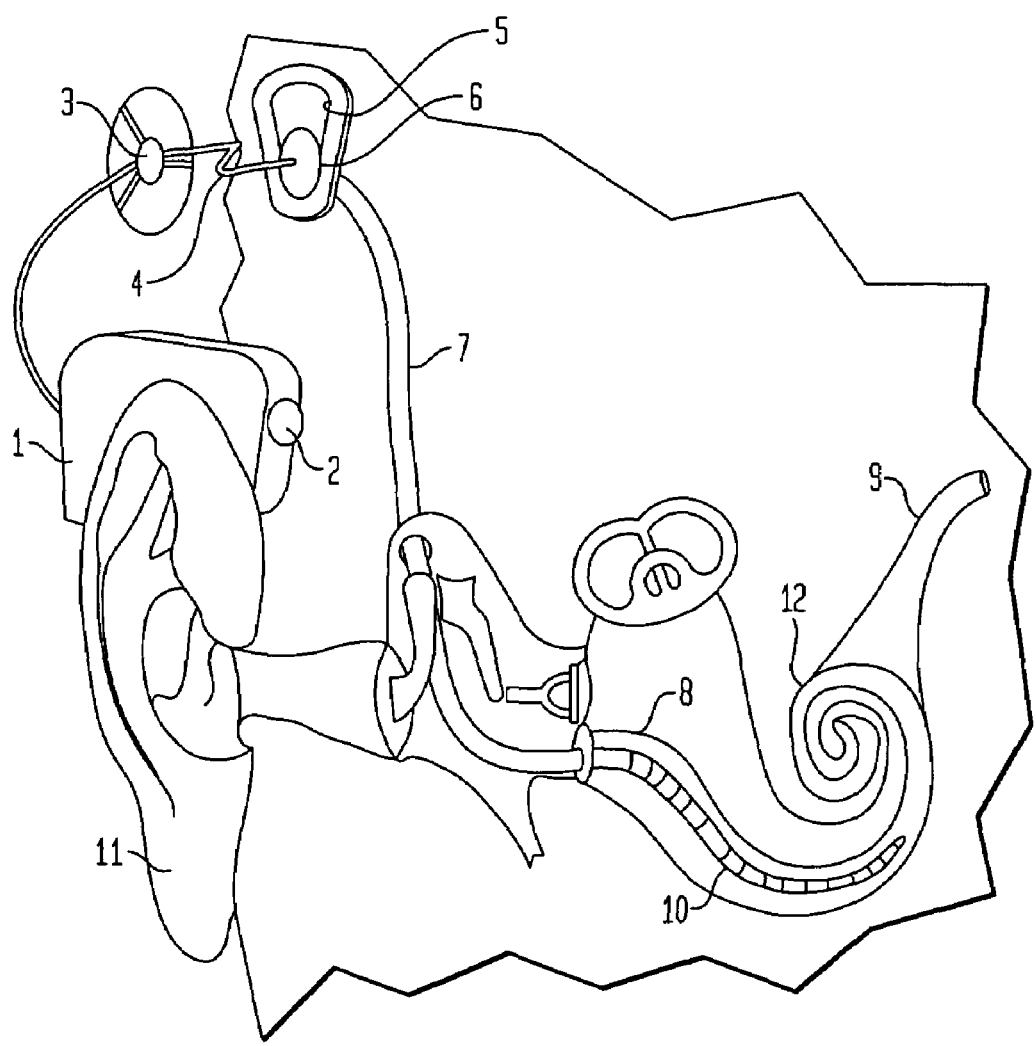
FIG. 1 is an illustration of a typical cochlear implant system.

FIG. 1 illustrates a typical cochlear implant system having an external component, including a speech processor 1, and an internal component including an implanted receiver and stimulator unit 6. The external component includes a microphone 2. The speech processor is in this illustration constructed and arranged so that it can fit behind the outer ear 11. Alternative versions may be worn on the body. Attached to speech processor 1 is a transmitter coil 3 which transmits the electrical signals to the implanted unit 6 via an RF link 4.

The implanted component includes a receiver coil 5 for receiving power and data from transmitter coil 3. A cable 7 extends from the implanted device 6 to the cochlea 12 and terminates in an electrode array 10. The signals thus received are applied by the array 10 to the basilar membrane 8 thereby stimulating the auditory nerve 9. The operation of the device shown in FIG. 1 is described, for example, in U.S. Pat. No. 4,532,930.

Thus, the RF link, which is in turn powered by the speech processor 1, provides power and data to the implanted device 6. The speech processor also processes sound signals received by microphone 2, so as to send appropriate processed audio information or stimulus and/or control commands to the implanted device 6. The precise details of speech processing are not necessary for an understanding of the present invention, and the skilled worker in the art will be aware that many such schemes have been used and proposed. Virtually all such schemes rely on patient specific data. For example, post implantation it is usual for the implanted electrodes in a multi-electrode array to be tested for function, and for the sound percepts which are generated by stimuli to particular electrode pairs to be determined. These electrode specific percepts used in conjunction with a stimulation strategy to generate a patient specific map. Different patients have different speech processing strategies, and different parameters within a given speech processing strategy. Further, each user may have a unique stimulus coding strategy. Other data may also be stored, for example alternative speech processing schemes and the user specific strategy for those schemes, or data of other types. All these data will be discussed as user specific parameters for the purposes of the discussion below, and are well understood by those skilled in the art.

Commercially available cochlear implant systems have in some cases a telemetry system in place. This allows for various parameters sensed by the implant to be sent back via the communications link to the speech processor. Conventional telemetry data may include data on the operation of the implant, as well as sensor data to assist in defining stimulus and speech processing strategies and for diagnostics.

Figure 2A:
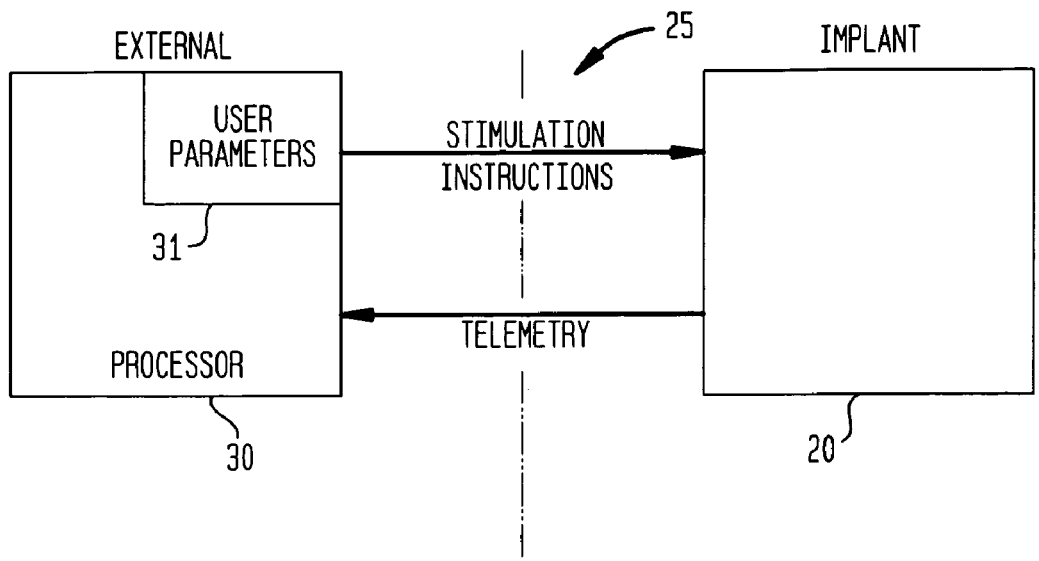
FIG. 2A illustrates the division of function within a prior art cochlear implant.

FIG. 2A illustrates the conceptual operation of a conventional device. The user parameters 31 are stored in non-volatile memory in the external processor 30. The external processor 30 communicates via communications link 25 with the implant 20. Instructions as to the electrical stimuli to be delivered are sent to the implant, and telemetry data is sent back from the implant, via communications link 25.

Figure 2B:
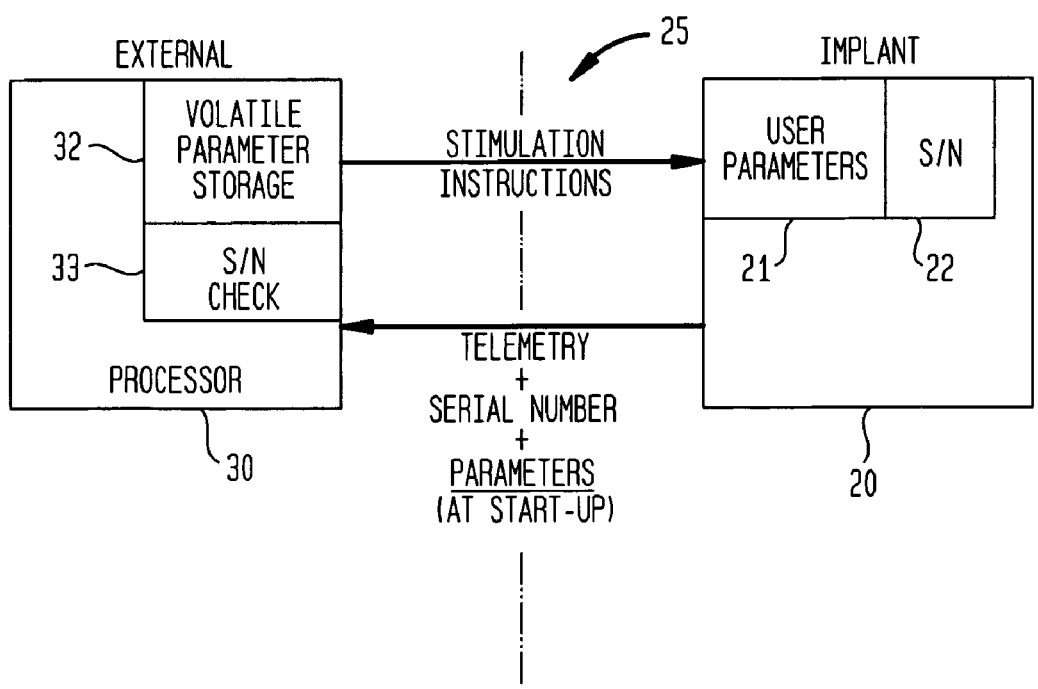
FIG. 2B illustrates the division of function within a cochlear implant device according to the present invention.

FIG. 2B illustrates the conceptual approach of the present invention. Implant 20 includes user parameters 21, and a serial number 22, stored in non-volatile memory. The parameters would be initially set using a programming mode using data derived from clinical and audiological tests, as is conventional. However, instead of this data being stored in the external processor 30, it is stored in the implant. It will be appreciated that the user parameters 21 could be in a coded format to minimise the data required to be downloaded during start-up. The serial number 22 could be implemented in various ways, including the use of a fixed serial number. An alternative would be a value set as a result of a handshake at start up with the external processor, so that the value is changed with each new start-up. Such mechanisms are well known in the communications field, and the exact form of interaction is not crucial. It is important however, that there is some form of on-going check, so that the external processor continues to send signals only when the correct implant is interoperating.

The processor 30 according to the present invention includes a volatile memory 32 for storing the user parameters downloaded during the start-up process. This may be strictly a volatile memory, or merely one which is reused. It is highly preferred that this data is not retained by the speech processor, and the processor operates only on data that is downloaded each time it is powered up and recognizes the implant. The external processor 30 also includes code 33 necessary to perform the on-going check of serial number, as discussed above.

As can be seen from FIG. 2, the communications link carries not only telemetry, but also serial number data and, at start up, the user parameters from the implant to the external processor. The link 25 carries processed audio information or stimulus and/or control commands, as well as signals relating to the on-going check of the connection.

As it is not simply a master/slave relationship, the external processor and implant need to complete a start up procedure each time the speech processor is turned on. A suitable procedure is as follows:

1. The speech processor is not receiving back telemetry signals, and so it sends an implant interrogation sequence.
2. The implant responds to the interrogation sequence.
3. The speech processor identifies the implant, for example model and number, and requests download of user parameters.
4. The speech processor configures itself according to the user parameters and implant data downloaded.
5. The speech processor starts signal processing and mapping, stimulus and/or command encoding based upon the downloaded data. A "handshake" with the implant is maintained continuously.

Step 5 may involve a simple low-rate handshake, for example an acknowledgement sequence sent for example, 100 ms or for the system at a rate low enough to identify when the communication link is broken, but not so low that the system does not recognise that a new device has been swapped. Alternatively, a higher rate handshake, such as a compliance telemetry response in each stimulus frame, could be used.

It will be appreciated the present invention can be readily applied to any implanted device required to operate with an external device to provide normal function. It will be apparent to those skilled in the art that variations and additions are possible within the general inventive concept.

The invention claim is:

1. A cochlear implant device comprising:
    an internal component implantable in a patient, comprising:
        a second memory having patient-specific parameters stored therein during a prior programming operation
        an electrode array configured to provide stimulation to a cochlea of the patient; and
    an external component configured to be worn by the patient comprising:
        a first memory adapted to have stored therein said patient-specific parameters for the patient, and
        a speech processor configured to download said patient-specific parameters from said second memory to said first memory, and to utilize said downloaded patient-specific parameters stored in said first memory to perform speech processing operations customized for the patient.

2. The device of claim 1, wherein said patient-specific parameters further comprise parameters specific to said internal component.

3. The device of claim 1, wherein said external component is configured to download said patient-specific parameters each time said external component initiates operations.

4. The device of claim 1, wherein said external component is further configured to verify that said patient-specific parameters stored in said first memory are the same as said patient-specific parameters stored in said second memory.

5. The device of claim 4, wherein said speech processor is configured to transmit speech processed signals to said internal component only when said patient-specific parameters stored in said first memory are the same as said patient-specific parameters stored in said second memory.

6. The device of claim 1, wherein said internal component is further configured to have stored therein a unique identifier representing said patient-specific parameters stored in said second memory.

7. The device of claim 6, wherein said unique identifier is a fixed identifier.

8. The device of claim 6, wherein said unique identifier is a dynamic unique identifier that changes at each new start-up of said external component.

9. The device of claim 6, wherein said external component is configured to download said unique identifier stored in said internal component concurrently with said patient-specific parameters.

10. The device of claim 9, wherein said external component is configured to perform periodic interrogations of said internal component to verify that said unique identifier stored in said internal component is the same as the unique identifier stored in said external component.

11. The device of claim 10, wherein said speech processor is configured to transmit speech processed signals to the internal component only when said unique identifier stored in said internal component is the same as the unique identifier stored in said external component.

12. The device of claim 1, wherein said first memory is a volatile memory.

13. The device of claim 1, wherein said speech processor is one of a plurality of interchangeable generic speech processors.

14. The implant of claim 1, wherein said patient-specific parameters comprise:
speech processing strategies.

15. The implant of claim 1, wherein said patient-specific parameters comprise:
stimulus coding strategies.

16. The implant of claim 1, wherein said patient-specific parameters comprise:
electrode mapping parameters.

17. An external component of a cochlear implant device, the implant having an internal component implanted in a recipient comprising: a second memory having patient-specific parameters specific for a recipient stored therein during a prior programming operation, and an electrode array configured to provide stimulation to a cochlea of the recipient, wherein the external component is configured to be worn by a recipient, and wherein the external component comprises:
a first memory adapted to have stored therein patient-specific parameters specific for the recipient; and
a speech processor configured to download said patient-specific parameters from said second memory to said first memory, and to utilize said downloaded patient-specific parameters stored in said first memory to perform speech processing operations customized for the recipient.

18. The external component of claim 17, wherein said patient-specific parameters further comprise parameters specific to said internal component.

19. The external component of claim 17, wherein said external component is configured to download a unique identifier stored in said internal component concurrently with said patient-specific parameters.

20. The external component of claim 17, wherein said external component is further configured to verify that said patient-specific parameters stored in said first memory are the same as said patient-specific parameters stored in said second memory.

21. The external component of claim 20, wherein said speech processor is configured to transmit speech processed signals to said internal component only when said patient-specific parameters stored in said first memory are the same as patient-specific parameters stored in said second memory.

22. The external component of claim 17, further configured to download a unique identifier stored in said internal component each time said external component initiates operation.

23. The external component of claim 22, wherein said unique identifier downloaded to said external component is a fixed identifier.

24. The external component of claim 22, wherein said unique identifier downloaded to said external component is a dynamic unique identifier that changes at each new start-up of said external component.

25. The external component of claim 22, wherein said external component is configured to perform periodic interrogations of said internal component to verify that said unique identifier stored in said internal component is the same as said unique identifier stored in said external component.

26. The external component of claim 25, wherein said speech processor is configured to transmit speech processing signals to said internal component only when said unique identifier stored in said internal component is the same as the unique identifier stored in said external component.

27. The external component of claim 17, wherein said external component is configured to be interchangeable with other external components.

28. The external component of claim 17, wherein said patient-specific parameters comprise:
speech processing strategies.

29. The external component of claim 17, wherein said patient-specific parameters comprise:
stimulus coding strategies.

30. The external component of claim 17, wherein said patient-specific parameters comprise:
electrode mapping parameters.

31. A cochlear implant comprising:
an internal component configured to have patient-specific parameters stored therein during a programming operation, wherein said patient-specific parameters are specific to a recipient of said cochlear implant;
a speech processor configured to be worn the recipient and to download said patient-specific parameters stored in said internal component, and to utilize said downloaded patient-specific parameters to perform speech processing operations customized for the recipient; and
an electrode array configured to provide stimulation to a cochlea of the recipient based on said customized speech processing operations;
wherein said speech processor is configured to download said patient-specific parameters prior to commencing said customized speech processing operations.

32. The implant of claim 31, wherein said speech processor is further configured to download said patient-specific parameters each time said speech processor initiates operations.

33. The implant of claim 31, wherein said speech processor is further configured to periodically interrogate said internal component to verify that the patient-specific parameters stored in said speech processor are the same as said patient-specific parameters stored in said internal component.

34. The implant of claim 33, wherein said speech processor is configured to transmit speech processed signals to said internal component only when the patient-specific parameters stored in said speech processor are the same as said patient-specific parameters stored in said internal component.

35. The implant of claim 31, wherein said internal component is further configured to have stored therein a unique identifier representing said patient-specific parameters stored in said internal component.

36. The implant of claim 35, wherein said unique identifier is a fixed identifier.

37. The implant of claim 35, wherein said unique identifier is a dynamic unique identifier that changes at each new start-up of said speech processor.

38. The implant of claim 35, wherein said speech processor is configured to download said unique identifier stored in said internal component concurrently with said patient-specific parameters.

39. The implant of claim 38, wherein said speech processor is configured to perform periodic interrogations of said internal component to verify that said unique identifier stored in said internal component is the same as said unique identifier stored in said speech processor.

40. The implant of claim 38, wherein said speech processor is configured to transmit speech processed signals to said internal component only when said unique identifier stored in said internal component is the same as said unique identifier stored in said speech processor.

41. The implant of claim 31, wherein said patient-specific parameters further comprise parameters specific to said internal component.

42. The implant of claim 31, wherein said patient-specific parameters comprise:
speech processing strategies.

43. The implant of claim 31, wherein said patient-specific parameters comprise:
stimulus coding strategies.

44. The implant of claim 31, wherein said patient-specific parameters comprise:
electrode mapping parameters.

45. A method of improving a patient's hearing comprising:
implanting an internal component of a cochlear implant into the patient;
storing patient-specific parameters particular to the patient into said internal component during a programming operation;
initializing a speech processor configured to be worn by the patient;
transferring said patient-specific parameters stored in said internal component to said speech processor;
performing speech processing operations customized for the patient based on said downloaded patient-specific parameters; and
stimulating a cochlea of the patient based on said customized speech processing operations.

46. The method of claim 45, wherein transferring said patient-specific parameters comprises:
interrogating said internal component with an interrogation sequence initiated by said speech processor;
said internal component responding to said interrogation sequence;
said speech processor identifying said internal component; and
copying said patient-specific parameters stored in said internal component to said speech processor.

47. The method of claim 45, further comprising:
storing a unique identifier in said internal component during said programming operation.

48. The method of claim 47, further comprising:
downloading said unique identifier stored in said internal component concurrently with the transfer of said patient-specific parameters.

49. The method of claim 48, further comprising:
said speech processor periodically interrogating said internal component; and
verifying that said unique identifier stored in said internal component is the same as said unique identifier stored in said speech processor.

50. The method of claim 49, further comprising:
said speech processor performing speech processing operations only when said unique identifier stored in said internal component is the same as the unique identifier stored in said external component.

51. The method of claim 45, further comprising:
said speech processor downloading said patient-specific parameters from said internal component each time said speech processor initiates operations.

52. The method of claim 45, further comprising:
verifying that said speech processor is interoperating with an internal component having stored therein the same patient-specific parameters as are stored in said speech processor.

53. The method of claim 52, further comprising:
said speech processor performing speech processing operations only when said patient-specific parameters stored in said speech processor are the same as said patient-specific parameters stored in said internal component.

54. The method of claim 45, wherein said patient-specific parameters comprise:
speech processing strategies.

55. The method of claim 45, wherein said patient-specific parameters comprise:
stimulus coding strategies.

56. The method of claim 45, wherein said patient-specific parameters comprise:
electrode mapping parameters.

57. A kit for providing stimulation to a recipient comprising:
an internal component configured to have patient-specific parameters stored therein during a programming operation, wherein said patient-specific parameters are specific to the recipient of said kit;
a first speech processor configured to be worn by the recipient and configured to perform speech processing operations customized for the recipient;
an electrode array configured to provide stimulation to a cochlea of the recipient based on said customized speech processing operations; and
a generic speech processor configured to be worn by the recipient and configured to replace said first speech processor, and configured to download said programmed patient-specific parameters upon initialization with said internal component, wherein said generic speech processor utilizes said downloaded patient-specific parameters in order to perform said customized speech processing operations based solely on said downloaded parameters.

58. The kit of claim 57, wherein said patient-specific parameters comprise:
speech processing strategies.

59. The kit of claim 57, wherein said patient-specific parameters comprise:
stimulus coding strategies.

60. The kit of claim 57, wherein said patient-specific parameters comprise:

electrode mapping parameters.

61. The kit of claim 57, wherein said generic speech processor is configured to download a unique identifier stored in said internal component concurrently with said patient-specific parameters.

62. The kit of claim 57, wherein said generic speech processor is further configured to verify that said patient-specific parameters stored in said generic processor are the same as said patient-specific parameters stored in said internal component.

63. The kit of claim 62, wherein said generic speech processor is configured to transmit speech processed signals to said internal component only when said patient-specific parameters stored in said generic speech processor are the same as said patient-specific parameters stored in said internal component.

64. The kit of claim 57, further configured to download a unique identifier stored in said internal component each time said generic speech processor initiates operation with said internal component.

65. The kit of claim 64, wherein said unique identifier downloaded by said generic speech processor is a fixed identifier.

66. The kit of claim 64, wherein said unique identifier downloaded by said generic speech processor is a dynamic unique identifier that changes at each new start-up of said internal component.

67. The kit of claim 61, wherein said generic speech processor is configured to perform periodic interrogations of said internal component to verify that said unique identifier stored in said internal component is the same as said unique identifier stored in said generic speech processor.

68. The kit of claim 67, wherein said generic speech processor is configured to transmit speech processing signals to said internal component only when said unique identifier stored in said internal component is the same as the unique identifier stored in said generic speech processor.

69. The kit of claim 57, wherein said generic speech processor is one of a plurality of interchangeable generic speech processors.

\* \* \* \* \*